United States Patent
Hayhurst

Patent Number: 5,810,848
Date of Patent: Sep. 22, 1998

[54] SUTURING SYSTEM

[76] Inventor: John O. Hayhurst, 14751 SE. Wanda Dr., Milwaukie, Oreg. 97267

[21] Appl. No.: 700,981

[22] Filed: Aug. 21, 1996

[51] Int. Cl.$^6$ .................................................. A61B 17/04
[52] U.S. Cl. ........................ 606/144; 606/139; 606/145; 606/232; 606/148
[58] Field of Search .................................. 606/139, 144, 606/145, 148, 232, 104, 72, 73, 75; 604/51, 43, 44, 89; 623/11; 600/32

[56] References Cited

U.S. PATENT DOCUMENTS

| | | | |
|---|---|---|---|
| 1,114,268 | 10/1914 | Kells | 604/43 |
| 3,103,666 | 9/1963 | Bone . | |
| 3,470,834 | 10/1969 | Bone . | |
| 3,875,648 | 4/1975 | Bone . | |
| 3,990,619 | 11/1976 | Russell . | |
| 4,006,747 | 2/1977 | Kronenthal et al. . | |
| 4,039,078 | 8/1977 | Bone . | |
| 4,121,487 | 10/1978 | Bone . | |
| 4,235,238 | 11/1980 | Ogiu et al. . | |
| 4,326,531 | 4/1982 | Shimonaka . | |
| 4,493,323 | 1/1985 | Albright et al. . | |
| 4,543,087 | 9/1985 | Sommercorn et al. | 604/43 |
| 4,568,329 | 2/1986 | Mahurkar | 604/43 |
| 4,590,928 | 5/1986 | Hunt et al. . | |
| 4,621,640 | 11/1986 | Mulhollan et al. . | |
| 4,669,473 | 6/1987 | Richards et al. . | |
| 4,738,255 | 4/1988 | Goble et al. . | |
| 4,741,330 | 5/1988 | Hayhurst . | |
| 4,899,743 | 2/1990 | Nicholson et al. . | |
| 4,968,315 | 11/1990 | Gatturna . | |
| 5,100,417 | 3/1992 | Cerier et al. . | |
| 5,219,335 | 6/1993 | Willard et al. | 606/164 |
| 5,250,055 | 10/1993 | Moore et al. | 606/148 |
| 5,269,809 | 12/1993 | Hayhurst et al. . | |
| 5,417,691 | 5/1995 | Hayhurst . | |
| 5,464,424 | 11/1995 | O'Donnell, Jr. | 606/228 |
| 5,549,631 | 8/1996 | Bonutti | 606/232 |
| 5,569,305 | 10/1996 | Bonutti | 606/232 |

FOREIGN PATENT DOCUMENTS

WO89/10096  11/1989  WIPO .

*Primary Examiner*—Michael Buiz
*Assistant Examiner*—Tina T. D. Pham
*Attorney, Agent, or Firm*—Hancock Meininger & Porter, LLP

[57] ABSTRACT

The suturing system includes a cannula that defines two adjacent lumens. One lumen carries a supply of anchor members that are joined together by a suture. The anchor members are moved by a supply rod, one at a time, from a lower lumen to an upper lumen. The upper lumen terminates in a sharpened tip that is pierced through tissue. The single anchor member that is moved into the upper lumen is then deployed into or behind the pierced tissue and the cannula is retracted. The rod for deploying the anchor member also temporarily blocks movement of additional anchor members from the lower to the upper lumen so that the surgeon can sufficiently tense the suture before piercing the tissue in an adjacent location and depositing a second anchor member. A series of anchor members joined by a continuous suture are deposited in this matter to suture together tissue. Also provided is a gun to which the cannula is mounted for one-handed operation of the system.

19 Claims, 4 Drawing Sheets

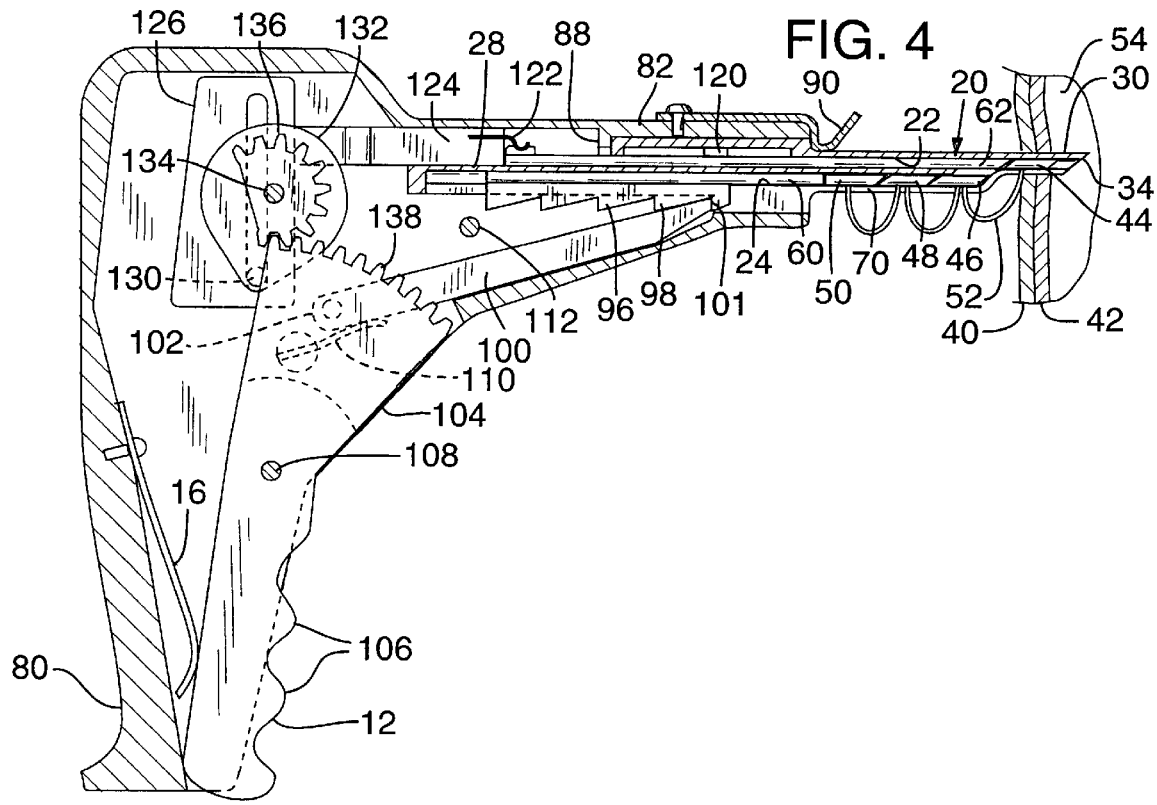
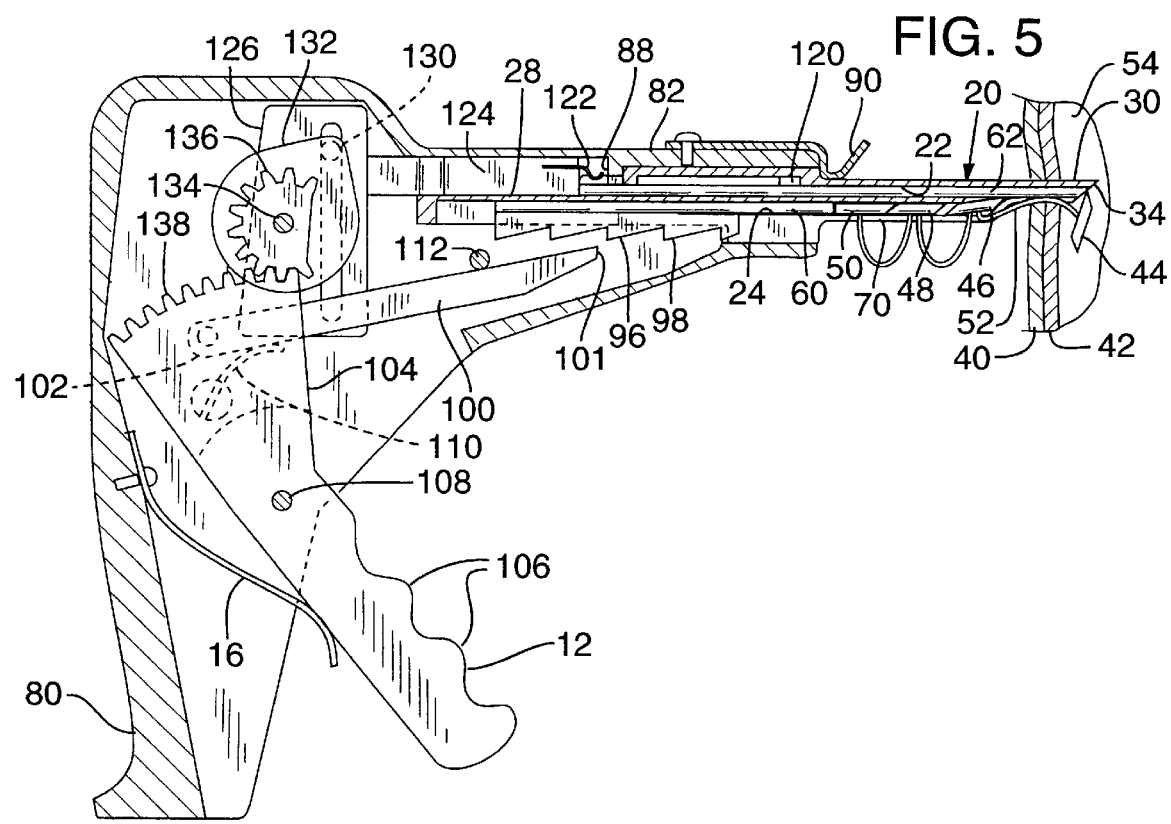

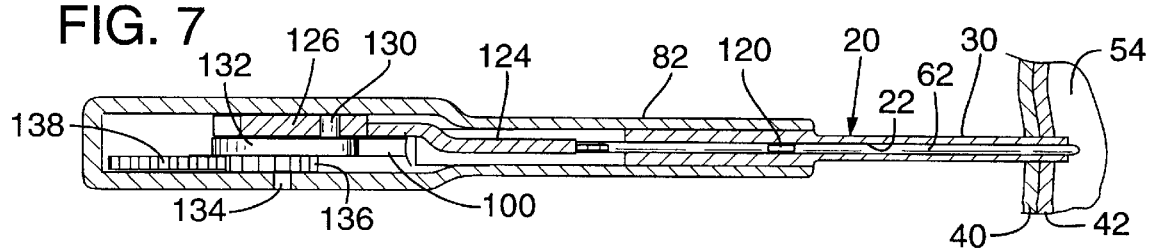
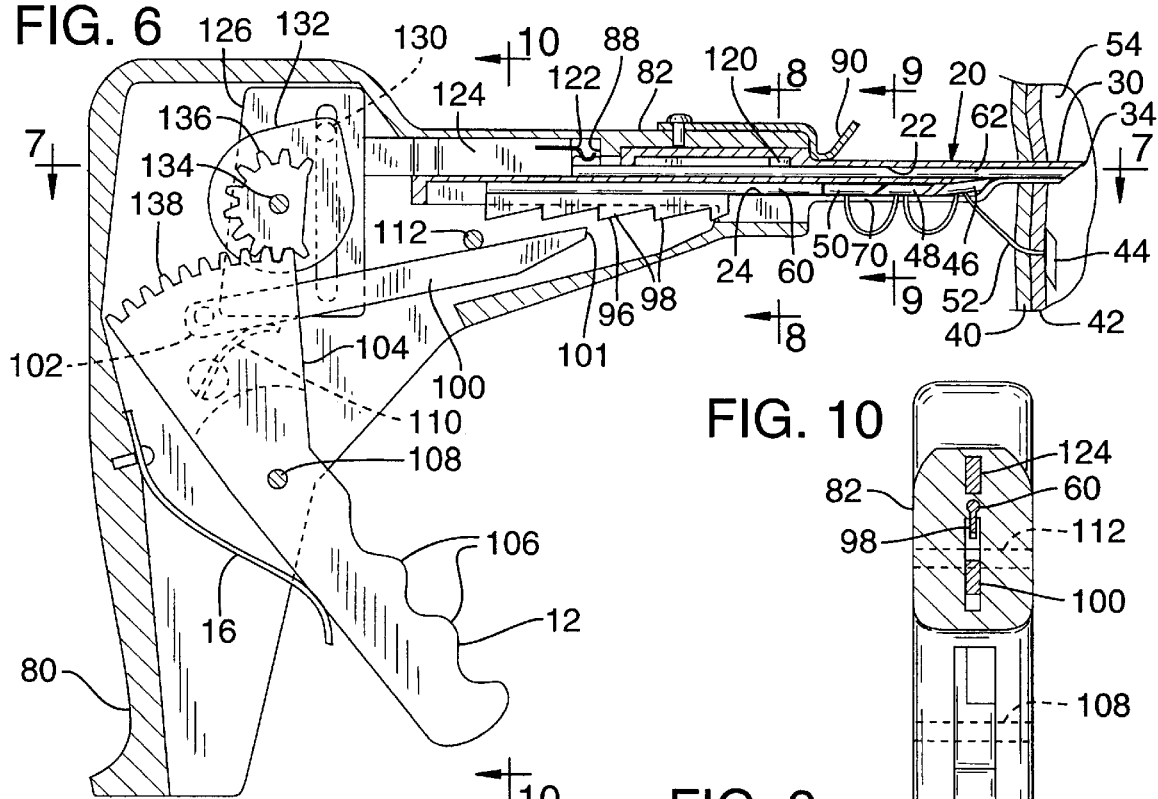
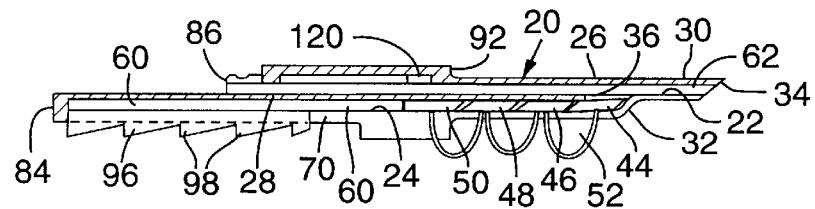

SUTURING SYSTEM

FIELD OF THE INVENTION

This invention relates to a system that is used for suturing together internal tissue or for attaching material to tissue.

BACKGROUND INFORMATION AND SUMMARY OF THE INVENTION

Surgeons are often faced with the task of reconnecting human tissue that is severed as a result of trauma or surgical procedures. One such technique is known as intestinal anastomosis, where portions of intestines are joined together. Reconnection can be carried out by suturing the tissue together. Another approach is to employ a device, similar to a stapler, whereby plastic, absorbable staples are pierced across the two portions of the tissue to be reconnected.

Certain soft tissues are not amenable to reconnection using sutures alone. In this regard, tensioning the suture once it is threaded through the tissue may cause the suture to cut through or pull out of the tissue.

The present invention provides a suturing system for deploying a series of somewhat rigid anchor members, which are connected by a suture, at spaced apart locations within or adjacent to human tissue. The anchor members remain joined by the appropriately tensed suture, thereby securely "stitching" together parts of tissue to be reconnected. The system is also useful for attaching material, such as a fine mesh, to damaged tissue to facilitate healing. The present invention is particularly adapted for use with surgical procedures that employ endoscopic techniques.

As one aspect of the invention, the deployment of the individual anchor members is readily controlled by the surgeon so that the spacing between each anchor member and the tension applied to the suture portion between each anchor member may be easily adjusted as the surgeon deems appropriate for the particular suturing procedure.

BRIEF DESCRIPTION OF THE DRAWINGS

FIGS. 3 and 4 are cross-sectional views, like FIG. 2, depicting the system as it is manipulated for moving one of the anchor members from a stored position into a position for that anchor member to be deployed distal to the tissue that is being sutured.

FIG. 5 is a cross-sectional view, like FIG. 2, showing the system manipulated so that an anchor member is caused to be deployed in tissue.

FIG. 6 is a cross section, like FIG. 2, showing the system ready to deploy into tissue a second in a series of anchor members.

FIG. 7 is a cross-sectional view taken along line 7—7 of FIG. 6.

FIG. 8 is a cross-sectional view taken along line 8—8 of FIG. 6.

FIG. 9 is a cross-sectional view taken along line 9—9 of FIG. 6.

FIG. 10 is a cross-sectional view taken along line 10—10 of FIG. 6.

FIG. 11 is a side view, partially in cross-section, showing the cannula of the present system.

DETAILED DESCRIPTION OF A PREFERRED EMBODIMENT

Figure 1:
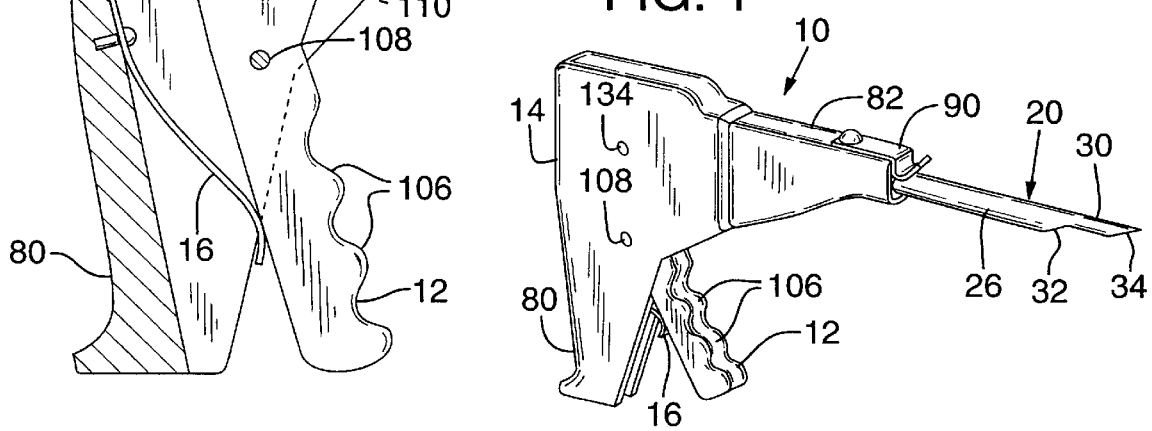
FIG. 1 is a perspective view of a preferred embodiment of the suturing system of the present invention.
Figure 12:
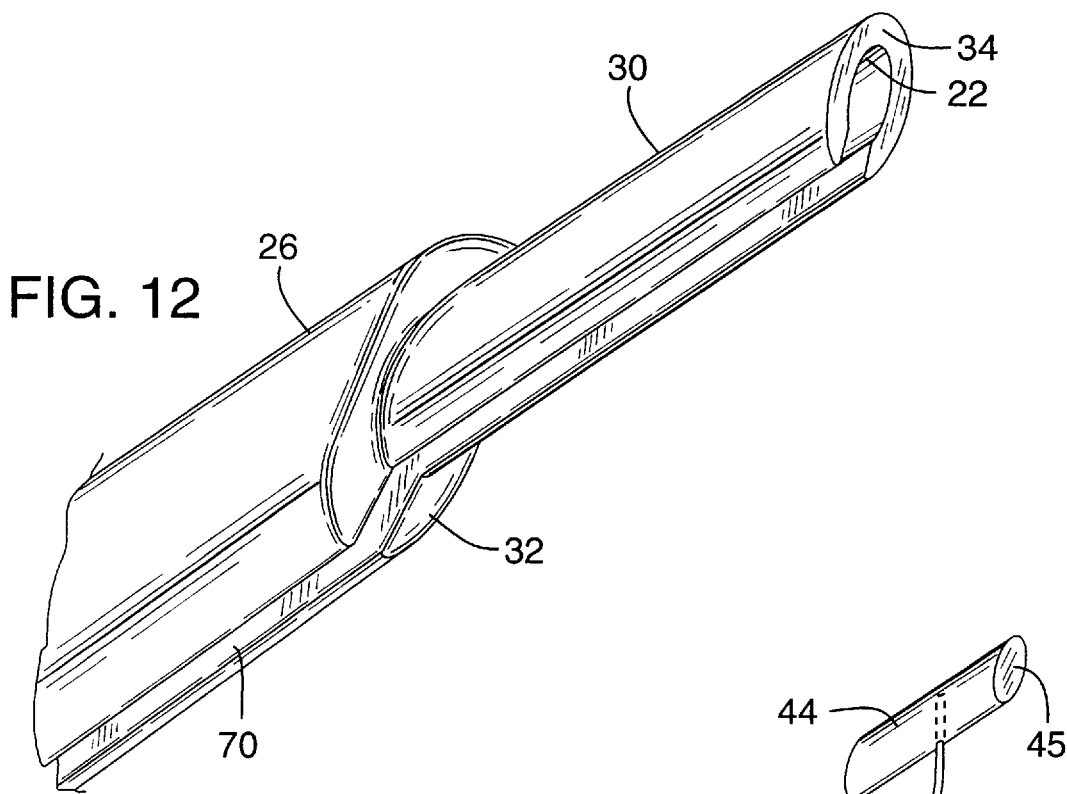
FIG. 12 is an enlarged perspective view depicting the tip of the cannula.

FIG. 1 depicts a perspective view of a preferred embodiment of the system in accordance with the present invention. The system generally includes a hand-held member, designating as a gun 10 to which a cannula 20 is removably attached. The gun 10 includes a handle 12 that is pivotally mounted to the gun body 14. A spring 16 normally urges the handle 12 to a released position (FIG. 1). The user may squeeze the handle 12 to overcome the spring and move the handle from the released to a second position, designated as the "loaded" position, as shown in FIG. 4.

In the course of moving the handle 12 from the released position to the loaded position and back, a pair of rods that are movably mounted within the cannula, and described more fully below, are controlled for expelling from the cannula tip 30, one at a time, a series of anchor members that are connected by a suture so that the anchor members and suture may be stitched into tissue.

The following portion of this description is directed to the cannula 20 and the above-mentioned rod action, followed by a description of a preferred embodiment of the gun 10 for operating the rods.

The cannula 20 may be formed of stainless steel or any other generally rigid material that can withstand sterilization. The cannula 20, as best shown in FIGS. 2–6 and 11–12, generally defines two adjacent lumens that, for convenience of the description, will be referred to as an upper lumen 22 and a lower lumen 24.

The lumens 22, 24 are defined by the outer wall 26 of the cannula and by a partition 28 (FIG. 11) that separates the upper lumen 22 from the lower lumen 24 for substantially the entire length of the cannula. The outer wall 26 of the cannula is configured to have a sloping transition 32 that defines the leading end (that is, to the right in the figures) of the lower lumen 24. The transition 32 is spaced from the leading end of the upper lumen 22. As a consequence, the tip 30 of the cannula comprises a single lumen, which is the extension of the upper lumen from the transition 32 to the leading edge 34 of the tip.

Near the tip 30 of the cannula, the lower and upper lumens are connected by a passage 36 (FIG. 11), which is essentially an opening in the partition 28 near the transition 32 of the cannula wall.

The leading edge 34 of the cannula is open and sharp to facilitate piercing the tip 30 of the cannula into tissue. In the figures, two tissue portions are shown, an outer tissue part 40 and an inner tissue part 42, which may be any soft tissue amenable to suturing. The line drawn between the outer and inner tissue can be considered as the area where the two tissues are reconnected by the suturing.

The lower lumen 24 is loaded with a supply of anchor members 44, 46, 48 and 50 that are joined by a continuous suture 52. The anchor members, four of which are shown in the figures, may be any of a variety of configurations and materials. In a preferred embodiment, the anchor members are formed of absorbable plastic. The anchor members are somewhat elongated, having a cylindrical cross-section with a diameter just slightly less than the diameter of the lower lumen 24 and upper lumen 22. In a preferred embodiment, the end faces of the anchor members, such as shown at 45, may be tapered to facilitate movement of the anchor members when deposited inside of tissue.

Figure 13:
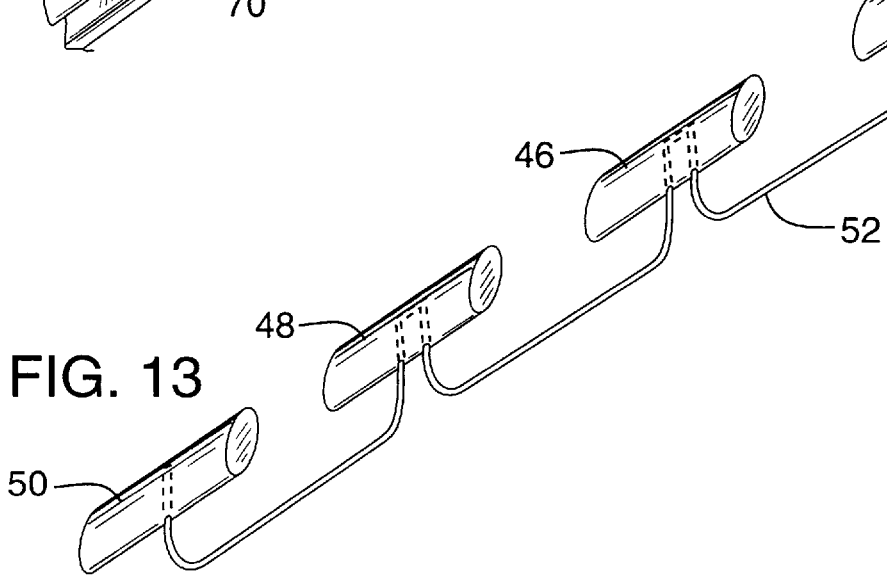
FIG. 13 is a perspective view of a series of anchor members joined by a suture prior to being loaded in the cannula of the present assembly.

One end of the suture 52 is fastened or knotted to a leading anchor member 44. In a preferred embodiment, the suture is also threaded twice through correspondingly shaped holes in the next two trailing anchor members 46, 48. The suture is fastened to the last anchor member 50 in the series of anchor members (FIG. 13). It will be appreciated that any of a number of anchor members can make up the series of anchor members and be loaded into the lower lumen 24. Moreover, the suture 52 may, instead of terminating in the last of the series of anchor members, extend outward of the cannula for manipulation by the user.

It is also contemplated that the suture 52 may be knotted or otherwise fixed at each of the anchor members, thereby to prevent movement of an anchor member relative to the suture. In another embodiment, the suture may be threaded through each anchor member in a way such that there is an interference fit between the suture and each anchor member so that when the suture is tensed sufficiently, and the anchor member is held in place, the suture can slide relative to the anchor member, thereby enlarging the spacing between the two held anchor members, as described more fully below.

Figure 2:
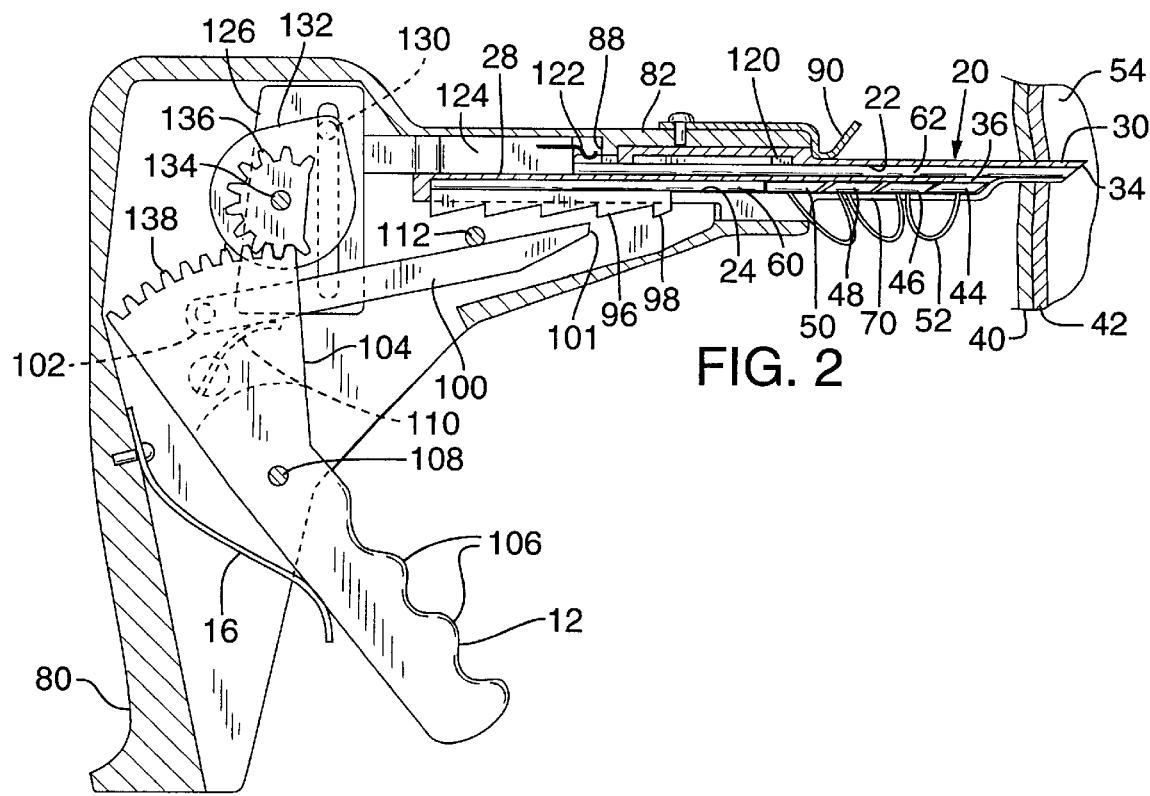
FIG. 2 is a side cross-sectional view of the system depicting the system ready for deploying in tissue a series of anchor members that are connected by a suture.

With a supply of anchor members 44, 46, 48, 50 stored in the lower lumen 24, the tip 30 of the cannula is then pierced through the tissue 40, 42 (FIG. 2). In the illustrated embodiment, the region to the right of the tissue 40, 42 represents a distal cavity in which the leading edge 34 of the tip 30 is disposed after piecing the tissue. It is contemplated, however, that after the cannula 20 is pierced into tissue, the tip 30 may be located to reside in soft tissue so that the anchor member deployed from the tip, as explained below, will anchor into the tissue itself. In any event, the region into which an anchor member is disposed will be referred to as the distal region 54.

Figure 3:
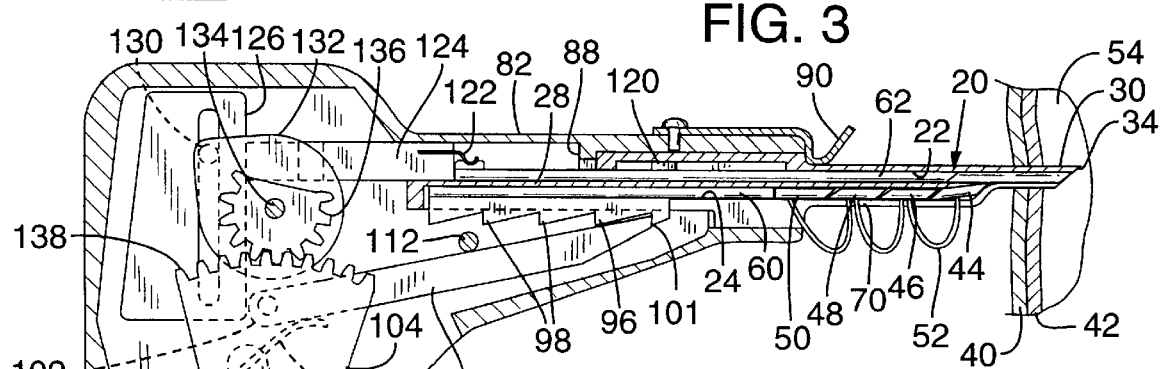

As mentioned, the deployment of the series of anchor members is generally facilitated by two rods. A supply rod 60 is disposed in the lower lumen 24. The supply rod 60 is a generally elongated cylindrical member that, when advanced toward the leading edge 34 of the cannula, pushes the series of anchor members so that the leading anchor member 44 slides along the transition 32, through the passage 36 and into the upper lumen 22, as best shown in FIGS. 3 and 4. Once the leading anchor member 44 is in the upper lumen, a generally elongated cylindrical deploy rod 62 that resides in the upper lumen is then extended toward the leading edge of the cannula to push the leading anchor member 44 out of the tip of the upper lumen to deposit that leading anchor member 44 in the distal region 54 of the tissue as shown in FIG. 5.

It is noteworthy that as the deploy rod 62 is advanced to push the leading anchor member 44 out of the tip 30 of the cannula, the deploy rod 62 simultaneously blocks the passage 36 that extends between the upper and lower lumens. Blocking the passage prevents the next, trailing anchor member 46 from moving into the upper lumen (see FIG. 6). As a result, the cannula 20, after the leading anchor member is deployed, can be relocated so that the tip 30 may be pierced again through the tissue while the trailing anchor member 46 (and all other anchor members behind it) is held in the lower lumen 24. Since the leading anchor member 44 and trailing anchor member 46 are thus held, respectively, by the tissue and deploy rod 62, the surgeon may, by spacing the next location for piercing the tissue, develop whatever amount of tension is desired in the suture between two deployed anchor members.

More particularly, tension is established in the suture 52 as the cannula 20 is retracted because the leading anchor member 44 is held against the tissue 42, and the trailing anchor member 46 is held within the lower lumen as a result of the blocking effect of the deploy rod 62. The cannula tip 30 is moved to a location where the suture 52 is sufficiently tense and again pierced through the tissue. The deploy rod 62 is then retracted to unblock the passage 36 so that the supply rod 60 can be further advanced by an amount sufficient to push the trailing anchor member 46 through the passage 36 and into the upper lumen 22 for subsequent deployment into the distal region by the deploy rod 62 in the manner as explained above in connection with the leading anchor member 44.

As noted earlier, the suture 52 may be fastened to each anchor member so that the amount of tension that may be applied between two held anchor members may be very large. If, on the other hand, the suture is connected to each anchor member by the above-described interference fit, a limited amount of tension may be applied (that is, up to an amount above which the suture would begin to slide relative to the anchor member). This sliding of the suture member, however, would be advantageous for the purpose of increasing the spacing between two adjacent anchor members, as deemed desirable by the surgeon. To this end, therefore, the cannula 20 may be retracted and pulled with enough force to cause the suture 52 to slip through the trailing anchor member 46, thereby extending the spacing between the leading and trailing anchor members.

An elongated slot 70 (See FIG. 12) is formed in the underside of the length of the cannula 20. Unlike the leading edge 34 of the cannula tip, the slot 70 is formed with no sharp edges. The cannula tip is manipulated so that the part of the suture 52 between each anchor member 44, 46, 48 will extend through the slot 70. The slot 70, therefore, prevents the suture 50 from contacting the sharpened edge 34 of the tip during piercing, thereby to avoid cutting the suture.

As noted earlier, the components comprising the suture system of the present invention are readily adapted for use in surgical procedures employing endoscopy. In this regard, the cannula 20 and rods 60, 62 have sufficient flexibility and size for use in such procedures.

It is contemplated that the ends of the supply rod 60 and deploy rod 62 that are distant from the tip of the cannula 20 can be manipulated by hand to carry out the suturing operation just described. Preferably, however, movement of the rods may be controlled by the above-mentioned gun 10 to which the cannula 20 and rods 60, 62 are mounted as shown.

The gun 10 comprises a grip 80 and a protruding barrel 82. The grip and barrel are generally hollow to house both a cannula 20 and the mechanisms for driving the supply rod 60 and deploy rod 62 in the cannula. More particularly, the butt end 84 of the cannula 20 is inserted into the barrel 82 by an amount such that the inner end 86 (FIG. 11) of the upper lumen 22 abuts a boss 88 (FIG. 6) that protrudes into the bore of the barrel 82. In this position, a spring clip 90 that is mounted to the barrel 82 snaps against a forward shoulder 92 that is formed in the upper lumen 22 (FIG. 11). With the clip 90 in place, the overall cannula 20, which otherwise fits snugly within the bore of the barrel, is held in place.

The clip 90 may be raised to easily remove the cannula 20 from the barrel 82 for the purposes of replacing or cleaning the cannula. It will be appreciated that any number of detent mechanisms may be employed for quick release and mounting of the cannula to the barrel of the gun.

The supply rod 60 has attached to its inner end a downwardly depending rachet 96 having a plurality of teeth 98 formed in its underside. The teeth 98 are periodically engaged by the end of a catch 100 that is part of the drive mechanism for incrementally advancing the supply rod 60 within the lower lumen 24 to sequentially move the anchor members from the lower lumen to the upper lumen 22 as mentioned above. The catch 100 is pivotally connected at its innermost end 102 to the inner end 104 of the handle 12. The inner end 104 of the handle 12 is contiguous with the outer end 106 of the handle that is grasped by the fingers of the user for moving the handle from the released position toward the loaded position. In this regard, the handle 12 is pinned to the gun body, as shown at 108 between the outer end 106 and the inner end 104. Consequently, as the handle 12 is swung (clockwise in FIG. 6) about the pin 108, the catch 100 is generally translated forward (that is, to the right in the figures) until the tip 101 of the catch 100 engages a tooth 98 of the ratchet.

The drive mechanisms of the gun 10 are sized and arranged so that as the handle 12 is moved from the released position (FIG. 2) to the loaded position (FIG. 4), the catch 100 will eventually bear against a tooth 98 of the ratchet 96 and advance the ratchet and attached rod by an amount sufficient for moving a single anchor member from the lower lumen 24 through the passage 36 and into the upper lumen 22.

The handle 12 also has fastened to it a leaf spring 110 that normally urges the catch 100 against a cylindrical guide 112 in the gun body 14 to ensure that the tip 101 of the catch engages a tooth 98 of the ratchet when the catch is advanced. When the catch is retracted (that is, when the handle 12 is released so that the spring 16 moves the handle into the released position), the spring 110 yields so that the catch tip 101 may move downwardly to slide over the ratchet, which is not retracted, thereby to have the tip 101 align with a next one of the gear teeth 98.

The drive mechanism of the present invention is configured so that as the supply rod 60 is advanced as just described, the deploy rod 62 is retracted into the upper lumen 22 by an amount sufficient to unblock the passage 36 so that the advancing supply rod is able to force a single anchor member through the passage into the upper lumen. In this regard, the deploy rod 62 is driven so that it is reciprocated within the upper lumen 22: generally retracted as the supply rod is advanced, and generally extended when the handle 12 is permitted to swing back (counter-clockwise) into the released position. To this end, the inner end of the deploy rod has a raised tab 120 attached thereto to protrude upwardly into a correspondingly shaped slot that is defined in the cannula 20 contiguous with the upper lumen 22. The slot and tab 120 arrangement guides movement of the rod 62 in the cannula 20.

The inner end 86 of the deploy rod carries another tab that is notched to receive a protruding end of a resilient spring clip 122, once the cannula 20 is mounted in the barrel 82 as described above. The spring clip 122 extends from an elongate, generally rectangular arm 124 that is attached to a follower plate 126. The follower plate 126 is housed within the gun and fits within the gun in a manner such that it is restricted to translational reciprocating motion forward and backward (that is, right and left in the figures) when driven as described next.

The follower plate 126 includes an elongated slot into which fits a cam pin 130 that protrudes from the eccentric portion of a cam 132 that is rotatably mounted about a shaft 134 next to the follower plate. Also mounted to the shaft 134 is a cam gear 136 that is fixed relative to the cam 132 so that the cam rotates whenever the cam gear 136 is rotated. The cam gear 136 is rotated by an arcuate rack 138 of gear teeth formed in the inner end 104 of the handle 12. More particularly, as the handle 12 is pulled from the released position into the loaded position, the resultant clockwise rotation of the rack 138 imparts counter-clockwise rotation to the cam gear 136 with which the rack teeth mesh. The counter-clockwise rotation of the cam gear pulls, via cam pin 130, the follower plate 126 and its attached arm 124 inwardly (to the left) so that the deploy rod that is connected thereto via clip 122 is retracted by an amount sufficient to unblock the passage 136.

If the handle is pulled completely into the loaded position (FIG. 4), the follower plate 126 and deploy rod 62 will be moved slightly forward to again block the passage, although only after an anchor member is moved into the upper lumen.

With reference to FIGS. 5 and 6, it will be appreciated that when the handle 12 is released so that the spring 116 urges the handle toward the released position, the resultant counter-clockwise rotation of the handle 12 will impart clockwise rotation into the cam gear 136 thereby, after a brief retraction, extending the deploy rod 62 through the upper lumen 22 to push any anchor member within the upper lumen 22 out of the tip of the cannula as described above.

FIG. 5 shows the system with the just-deployed anchor member 44 in the tissue distal region 54. FIG. 6 shows the system after the cannula tip 30 is retracted from the tissue, moved to an adjacent location (with the suture between the two anchor members 44, 46 sufficiently taut), and the tip 30 pierced into tissue, ready for deployment of the next anchor member 46.

Figure 14:
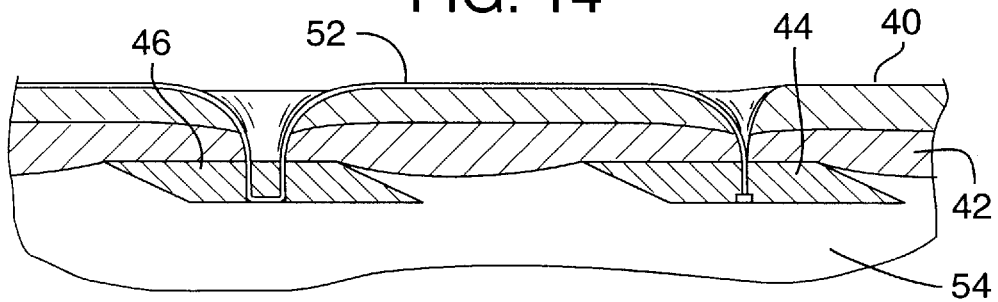
FIG. 14 is a cross-sectional enlarged view showing two of the series of anchor members deployed in tissue.

FIG. 14 shows an enlarged view of a deployed leading anchor member 44 and one trailing member 46 in the distal region 54 of the above-mentioned tissue 40, 42. The anchor members 44, 46, once deployed, tend to rotate as the suture is tensed, thereby providing a generally perpendicular orientation with the suture at the point the suture contacts the anchor member. As a result, the maximum resistance to movement back through the tissue is provided.

It will be appreciated that although outer tissue is depicted at 40 FIG. 14, that element could be other material, such as a fine, absorbable mesh material often used for repairing internal tissue. Put another way, the suturing system of the present invention may be used for stitching any material to human tissue.

Having described and illustrated principles of the invention with reference to preferred embodiments, it should be apparent that the invention can be further modified in arrangement and detail without departing from such principles.

The invention claimed is:

1. A suturing system, comprising:
   a cannula having a tip and defining a first lumen and a second lumen that are joined by a passage that extends between the first and second lumens near the tip of the cannula;
   a leading anchor member inside of the first lumen near the tip of the cannula;
   a trailing anchor member inside the second lumen and movable from the second to the first lumen through the passage;
   a suture connected between the leading and trailing anchor members; and a rod disposed in the first lumen and movable therein for pushing the leading anchor member out of the tip of the cannula and for blocking the passage that extends between the first and second lumens thereby to prevent the trailing member from moving from the second to the first lumen through the passage.

2. The system of claim 1 wherein the movable rod is retractable in the first lumen by an amount sufficient to unblock the passage between the first and second lumen so that the trailing anchor member may move through the passage.

3. The system of claim 1 including a third anchor member inside the second lumen and movable from the second to the first lumen through the passage and wherein the suture is also connected between the trailing and third anchor members.

4. The system of claim 1 wherein the tip of the cannula has a sharpened leading edge for piercing tissue, and wherein the tip also has a slot formed therein and into which slot the suture fits so that the suture does not contact the leading edge of the cannula tip.

5. The system of claim 2 including a second rod disposed in the second lumen and movable therein for pushing the trailing anchor member from the second lumen through the passage to the first lumen.

6. The system of claim 1 wherein an end of one of the lumens is spaced from the tip of the cannula thereby to define the tip of the cannula as comprising a single lumen.

7. The system of claim 6 wherein the tip has defined therein a slot sufficiently wide to permit a suture to extend out of the tip through the slot.

8. A method of deploying at a distal region of tissue a series of anchor members that are connected by a suture, comprising the steps of:

placing the series of anchor members in a cannula that has a tip for piercing tissue to penetrate to the distal region of the tissue;

piercing the tissue to locate the tip of the cannula near the distal region of tissue;

moving a deploy rod within a first lumen of the cannula for moving a first in the series of anchor members out of the tip to the distal region;

preventing with the deploy rod a second in the series of anchor members from moving out of the cannula tip while;

retracting the cannula to tense the portion of the suture that is between the first and second anchor members;

piercing the tissue to locate the tip of the cannula near the distal region of tissue; and moving the second anchor member out of the tip to the distal region.

9. The method of claim 8 including the step of moving a supply rod in a second lumen of the cannula for moving the second anchor member from the second lumen and into the first lumen thereby to permit the deploy rod to move the second anchor member out of the tip to the distal region.

10. A cannula system for deploying at a distal region of tissue a series of anchor members that are connected by a suture, comprising:

an elongated cannula having a tip and separate first and second lumens defined therein;

the cannula having a passage defined therein that connects the first and second lumens and is sized to permit passage of a single anchor member at a time between the two lumens and;

wherein the tip has a leading edge having defined therein a slot sufficiently wide to permit a suture to extend out of the tip through the slot.

11. The system of claim 10 wherein an end of one of the lumens is spaced from the tip of the cannula thereby to define the tip of the cannula as comprising a single lumen.

12. The system of claim 10 wherein the tip leading edge is sharp and wherein the slot is formed without sharp edges.

13. A cannula system for deploying at a distal region of tissue a series of anchor members that are connected by a suture, comprising:

an elongated cannula having a tip and separate first and second lumens defined therein;

the cannula having a passage defined therein that connects the first and second lumens and is sized to permit passage of a single anchor member at a time between the two lumens; and further comprising:

a deploy rod movably mounted in the first lumen; and a supply rod movably mounted in the second lumen.

14. The system of claim 13 further comprising:

a gun to which the cannula is removably mounted, the gun including:

drive means for advancing the supply rod through the second lumen and for reciprocating the deploy rod in the first lumen.

15. The system of claim 14 wherein the drive means includes:

a handle pivotally mounted to the gun;

a ratchet connected to the supply rod;

a catch connected between the handle and the ratchet to move with the handle and to bear against and advance the ratchet thereby to advance the supply rod through the second lumen.

16. The system of claim 14 wherein the drive means includes:

a handle pivotally mounted to the gun;

a cam follower connected to the deploy rod; and a cam connected between the handle and the cam follower to move with the handle and to reciprocate the cam follower thereby to reciprocate the supply rod in the first lumen.

17. The system of claim 16 wherein the drive means further includes:

a ratchet connected to the supply rod; and a catch connected between the handle and the ratchet to move with the handle and to bear against and advance the ratchet of the supply rod thereby to advance the supply rod through the second lumen.

18. The system of claim 16 wherein the drive means further comprises a spring for urging the handle to move from the second to the first direction.

19. The system of claim 17 wherein the handle is movable through a cycle defined by movement from a first position to a second position and back to the first position, and wherein the drive means is for advancing the supply rod through the second lumen and for reciprocating the deploy rod in the first lumen as the handle is moved through the cycle.

* * * * *